(12) United States Patent
Faul

(10) Patent No.: US 8,224,423 B2
(45) Date of Patent: *Jul. 17, 2012

(54) MEANS OF TRACKING MOVEMENT OF BODIES DURING MEDICAL TREATMENT

(75) Inventor: Ivan Faul, Boulder, CO (US)

(73) Assignee: Boulder Innovation Group, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,850

(22) Filed: Jun. 18, 2010

(65) Prior Publication Data

US 2011/0152677 A1   Jun. 23, 2011

Related U.S. Application Data

(63) Continuation of application No. 10/808,459, filed on Mar. 25, 2004, now Pat. No. 7,742,804.

(60) Provisional application No. 60/457,567, filed on Mar. 27, 2003.

(51) Int. Cl.
*A61B 5/05* (2006.01)
*A61N 7/00* (2006.01)

(52) U.S. Cl. ............ 600/427; 600/414; 600/415; 601/2
(58) Field of Classification Search ............... 600/411, 600/424, 414, 417, 426, 427, 407, 415, 595; 601/2; 356/496
See application file for complete search history.

(56) References Cited

U.S. PATENT DOCUMENTS

| 5,782,771 | A | * | 7/1998 | Hussman ................ 600/478 |
| 5,907,395 | A | * | 5/1999 | Schulz et al. ............ 356/139.03 |
| 6,094,007 | A | * | 7/2000 | Faul et al. ................ 313/512 |
| 2002/0193685 | A1 | * | 12/2002 | Mate et al. .............. 600/424 |

* cited by examiner

*Primary Examiner* — Long V. Le
*Assistant Examiner* — Katherine Fernandez
(74) *Attorney, Agent, or Firm* — The Marbury Law Group PLLC

(57) ABSTRACT

During preprogrammed medical treatment and remote controlled surgery tracking the movements of the body being treated and integrating those tracked movements with the preprogrammed/remote controlled treatment to arrive at an integrated modified treatment track and following that modified track during the treatment. The treating instrument may be a solid scalpel or high-energy radiation, such as X-rays, ultra sound, laser beams or the like.

31 Claims, 4 Drawing Sheets

MEANS OF TRACKING MOVEMENT OF BODIES DURING MEDICAL TREATMENT

RELATED APPLICATIONS

This application is a continuation of U.S. patent application Ser. No. 10/808,459 filed on Mar. 25, 2004, issued as U.S. Pat. No. 7,742,804, which claims the benefit of priority to U.S. Provisional Application Ser. No. 60/457,567, file Mar. 27, 2003 the entire contents of both of which are incorporated herein by reference.

FIELD

This invention is directed to the art of tracking the movement of objects, especially the involuntary movement of internal organs, or structural features, or the like, as a function of body movements cause by a patient's breathing or other voluntary or involuntary movement.

BACKGROUND

It is widely known that internal tumors can succumb to radio surgery and that kidney stones can be broken up into gravel by impinging ultra sound energy on them. Tumors in the thoracic cavity, or elsewhere in the body can be attacked by impinging laser, X-rays, or other high-energy radiation beams on them with sufficient power to kill the tumor cells. (Hereinafter, the term X-ray will be used in a generic sense to encompass many different kinds of radiation beams, such as X-rays, gamma rays, laser beams, ultra sound, and other similar radiation scalpels/tools).

Similarly, stones accumulated in the kidney, gall bladder and the like can be treated with other radiation beams, such as ultra sound, in order to break up the stones into gravel that is small enough to pass out of the patient's system. It is obvious that, if the direction of the high-energy radiation beam is not exactly where it is supposed to be, even if it is off very slightly, the consequences are that the procedure is either ineffective or not completely effective. That is, for example, either that the entire tumor is not destroyed, or rendered necrotic, (because the high energy X-ray beam doesn't reach to the edge of the tumor) or normal, healthy tissue is destroyed, or rendered necrotic, (because the X-ray beam impinges on tissue outside the periphery of the tumor). Therefore, technicians go to extreme lengths to insure that the X-ray beam is properly focussed exactly where the tumor, or other feature being treated, is.

It will be clear, however, that the patient being treated is breathing throughout the high-energy radiation treatment. Thus, the thoracic cavity (or other locations under treatment) is almost constantly moving as a function of normal breathing. Further, there is the risk that the patient will inadvertently sneeze or cough during treatment, which would severely impact on the accuracy of the impingement of the high-energy radiation. As the patient breathes, his chest moves and thus the alignment of the X-ray beam can move from being focused directly on the whole of the tumor, or other feature, to being off its target to a greater or lesser extent. The difference between on-target and slightly off-target need not be great. Even if the offset is very small, that difference can be critical to the success or failure of the treatment such as resection, or rendering the impinged tissue necrotic, or other treatment.

This situation is equally true for remote controlled and so called "surgeonless" operations that employ a solid scalpel rather than a radiation scalpel, such as a high energy X-ray beam. The scalpel is wielded by a remotely controlled machine that has been preprogrammed to follow a specific predetermined track or course, if the body being worked on moves during surgery, but the preprogrammed track has not been programmed to compensate for this movement, the scalpel will cut in the wrong place, at least part of the time. Also, when a remotely located surgeon is directly controlling the scalpel via remote-controlled means, and no preprogramming exists, real-time feedback of patient body motion is required to indicate to the remotely located surgeon, or to automated surgical equipment, that the patient or its organs have moved.

It is known in the surgical field that certain forms of surgery, particularly computer operated cranial image guided microneurosurgery, can be greatly assisted and improved by independently tracking the movements of a scalpel or probe while the functional ends of these instruments are out of line of sight of the surgeon. In this technique, these movements of the scalpel, or the like, are matched to the feature of the body that is being resected or rendered necrotic as it appears on a previously taken image of the portion of the intracranial tissue that is being resected or rendered necrotic (that is, the tumor). Thus, the probe or knife can be made to follow the contours of the diseased tissue as shown on a previously taken MRI, or the like, even where the surgeon cannot directly see the diseased tissue. Clearly it is very important that the patient's head be maintained absolutely still during the surgery, and this has been accomplished by severely clamping the head in suitable restraints prior to and during surgery. However, it is not always possible to maintain the cranium absolutely still during extended surgery.

It is also known (see U.S. Pat. No. 6,501,981 for example) to carry out treatments of internal features of a body while compensating for the inadvertent, or intentional, movement of the body during surgery. This reference discloses that this compensation is accomplished by periodically generating positional data about the internal target structure or feature that is being treated, continuously generating position data about the position of markers operatively associated with the body but positioned outside the body, and generating a correspondence between these sets of data.

As with most, if not all, medical instrumentalities, it is undesirable to employ an instrumentality with one patient that has been used by another patient. Further, it is important to use instrumentalities in connection with a patient that do not significantly adversely affect the treatment itself. In another embodiment . . . .

BRIEF SUMMARY

It is an object of this invention to provide apparatus for improving the accuracy of surgeonless treatment of internal features of a body of an animal, particularly a human.

It is an additional object of this invention to provide means for modifying preprogrammed surgical operations (solid or radiation scalpel) to account for movement of the patient's body during surgery.

It is a further object of this invention to provide means, that are auxiliary to preprogrammed surgery, to cause the movement of the surgical tool, or other operating tool, more accurate than has been possible by following the teachings of the prior art.

It is a still further object of this invention to provide disposable means for determining the movement of the patient and integrating such movement with preprogrammed treatment tracks.

Other and additional objects of this invention will become apparent from a consideration of this entire specification and claims.

In accord with and fulfilling these objects, one important aspect of this invention comprises the disposition of disposable markers at several different specific locations on the exterior of the portion of the body being treated and that is subject to movement during surgery. For example, such a body portion can be the chest cavity or the lower abdominal area, or the cranium. The spatial locations and orientations of these respective markers are each tracked with great accuracy in relation to a predesignated three-dimensional coordinate system that is fixed in space, such as the operating room. If the surface being tracked has been mapped during breathing, such as breathing with or without anesthesia, prior to the time of treatment with high-energy radiation or a remote controlled scalpel, that prior mapping can be integrated into the predetermined path to be followed by the scalpel (solid or radiation). Further, the prior tracked breathing movements can be compared to breathing movements being tracked during surgery and any differences superimposed on the predetermined movement tracking input to the surgical path. The direction as well as the power of the high energy radiation scalpel, or of the remotely controlled solid scalpel, or the like, is continually adjusted based on the instantaneous positions and orientations of the external markers so that the diseased tissue that is sought to be resected or rendered necrotic is substantially the only target to the greatest extent possible. There exists certain commercially available software, for example from Boulder Innovation Group, Inc., of Boulder, Colo., that is capable of performing these tracking activities both before and during surgery. The software used to track these movements is, of course, and integral part of the instant invention. This invention would not be operative without such software part of the instant invention. However, the software itself in not invented here, only its use in combination with disposable supports for the radiation emitters and in combination with certain optical fibers and certain emitters, in the instant method.

In order to map the motion of a surface, including a constantly moving surface such as a chest cavity that is moving because of breathing, it is necessary to provide receiver means where the emissions from LEDs or the like are received and the results of such reception converted to locations and direction vectors of the emitters. Where the emissions are radiation in the electromagnetic spectrum wavelengths, it is common to use as a receiver a three (3)-camera array to insure accurate location calculation of the transmitted information. While three-camera arrays are commonly used with LEDs emitters, two-camera arrays as well as a one-camera array system are also on the market. Since the receiver means is not per se inventive here, the generic term, "receiver" will be used to encompass and disclose all receiver arrays.

A receiver system is disposed within line of sight of the emitters so that emissions from the emitters can be picked up by the receivers and thereby are adapted to be converted into positions and direction vectors of the markers. The positions and direction vectors of the markers as so determined are then converted into a map of the moving outside of the body being worked on. When the emitters emit electromagnetic radiation, the receiver means may comprise one or more cameras that work together to place the emitters in their correct location so that constantly changing map of is established In one important feature of this invention, the means by which the marker is attached to the outside of the body is disposable. By using disposable markers the risk of transmitting infections and the like is substantially reduced, if not eliminated entirely. However, under certain circumstances, it is considered to be within the scope of this invention, although not preferred, for the means by which the markers are attached to the outside body surface(s) to be reusable. Although the preferred commercial embodiment of this invention may employ disposable markers, disposability is not an indispensable feature of all aspect of this invention.

Although a single marker may be used in the instant invention, it is preferred to use a plurality of markers. (As used hereinafter, the terms "marker" or "markers" should be considered to encompass both a single marker and a plurality of markers depending on the context in which the words are used. The use of singular or plural should not be considered to be a limitation.) The markers that are disposed on the patient's body are suitably radiation-emitting devices, such as a light emitting diode (preferably emitting light in the visible red and invisible infrared wavelengths). Such devices are often referred to as LEDs, even though they may not emit visible light. Alternatively, or in combination, a device that responds to a magnetic field, or a reflector of light (visible or not), or an emitter of visible light, or a laser diode, or their equivalents, can be used. Collectively the various markers are sometimes hereinafter referred to as "emitters". Nothing contained herein, however, should be construed as limiting the word, "emitter" to LEDs or the like. Rather, emitters should be construed to mean any means of conveying the location and direction vector of a marker relative to a controller. As used herein, the term "signal" is intended to mean whatever means is employed to communicate between the marker and the controller, such as for example, emitted radiation, reflection, disruption of a magnetic field, etc.

Emitter markers usually require a power source in order to enable them to emit radiation. Thus, the emitter is usually required to have battery power attached thereto, or to be attached to an outside source of electric power. A reflecting emitter, of course, does not require electric power input. It merely requires a reflective material disposed on an exposed surface and a beam of radiation that will be reflected onto a suitable receiver that will convert the reflected radiation into the position and orientation of the marker. An element that produces a magnetic signal can be powered by an electromagnet, in which case it must have access to a source of power, such as a battery or external line current, or it can be powered by a permanent magnet and therefore does not need a power source to enable it to operate. Alternatively, the marker(s) can be an electromagnetic sensor that responds to an externally generated and applied magnetic field. Other similar radiating markers are well known, per se, and will be apparent to those of ordinary skill in this art. The above referred to markers are merely exemplary.

Where external power is required, the marker must be provided with means of being electrically connected to a suitable power source. For example, a conventional connector or clip can be used. It is appropriate for the power connector to be attached directly to the marker in need of a power source. The marker is also directly attached to an element, preferably a disposable element, that can be adhered, in a relatively fixed location and orientation, to the patient's skin. The marker/support element combination is positioned such that the transmissions therefrom can be accurately received by a receiver means that will accept transmission from the emitter. From the direction; and possibly the strength, of the received radiation, it is possible to calculate the exact location and direction vector of the emitter/marker. By very accurately tracking a plurality of emitters, it is possible to define the motion of the surface supporting the emitters (the chest for example), such as movement that results from the patient's breathing. By tracking the emissions of the markers over short time intervals, it is possible to track and map movement of the surface as it is occurring. This information can then be integrated with the preprogrammed the path of the surgeonless scalpel/high energy radiation on a substantially instantaneous basis thereby substantially constantly adjusting the surgical path to account for the motion of the surface.

In a preferred embodiment of this invention, the emitter is an LED that emits radiation in the visible red or invisible infrared region of the spectrum. There are two preferred means of using such LED emitters in this invention. In the first embodiment, the LEDs are attached directly to the skin of the patient and are disposed at an angle such that their transmitted radiation is principally directed to a camera array, comprising at least one camera that is adapted to receive such transmissions and that is mounted in a fixed location. The LEDs can be fired in a predetermined sequence so that the calculating software knows which LED has fired at any specific time, and therefore which location on the patient's body is being tracked. Alternatively, the various LEDs can be selected to emit radiation of different wavelengths. This too can be a means of discriminating between emitters. If different wavelength emissions are used, all of the emitters may be fired simultaneously because discrimination is a function of the wavelengths being emitted. Alternatively, LEDs can be fired simultaneously, using the same wavelength, provided that software that differentiates between simultaneously firing emitters is employed.

In this embodiment, LEDs that are attached to the patient's skin must be operatively associated with a power source. The power source can be a battery, but more preferably will be a line current, which means stringing an electrically conducting wire across the patient. This causes two potential problems that must be taken into consideration by the operator. First, there is the danger of patient leakage current exceeding that specified by medical regulatory bodies by contact with the electrical conductor in use. The second is the fact that such conductive wires are quite opaque to most radiation. Therefore, the wires themselves can severely interfere with the accuracy of the operation by attenuating the high energy treating radiation that is being impinged on the patient.

An alternative and preferred embodiment is to position the LED(s), and their power supply, away from the patient and string optical fibers from the LEDs to positions on the skin of the patient. As these remote LEDs fire, the light is transmitted through the optical fibers to an exact location on the skin of the patient from which it is projected toward the camera array that is fixedly positioned according to this invention. The substantial advantages of this embodiment are twofold. First, no electrical wiring is in contact with the patient thereby eliminating the risk of exceeding patient isolation requirements. Second, where the scalpelless surgical tool is high energy X-radiation, an LED can be selected such that it can cooperate with optical fibers that are more transparent to the high energy radiation. While all optical fibers are more transparent to high-energy radiation than are solid electrical wires, plastic optical fibers, especially methyl methacrylate fibers, attenuate infrared light transmitted through it more than they attenuate visible light. In the preferred embodiment, plastic optical fibers are preferably used with visible red LEDs or other visible light sources, and glass optical fibers are preferably used with infrared LEDs or laser diodes. Glass fibers are more opaque to high energy radiation than is plastic fibers.

In some operations, it has been found to be efficient to employ a combination of mensuration techniques, both as a double check and in order to insure that all movements are accurately determined. For example, one could use a combination of LED electromagnetic radiation emission and magnetic field generation. Where optical fibers are used to transmit the electromagnetic radiation from a remote source into energy being beamed to a camera, the optical fibers will not interfere with the magnetic field based information.

The element supporting the emitter, reflector, or the like, may itself be made of a material that reflects the movement of the surface that it is attached to. The support material may be such that tracking the movements of the emitter(s), or the like, necessarily tracks the supporting element and, through the supporting element, tracks the movement of the spot on the surface to which the supporting element/emitter(s) is attached.

While the element attaching the emitter to the moving surface being tracked must be such that it tracks the movement of the surface substantially identically, in a preferred embodiment of this invention, it must also be as inexpensive as possible because it is preferably disposable. Generally speaking, a paper or cardboard supporting element will not serve in this application because, although these materials are very inexpensive, they are also is not particularly stable. In these cases, the movement of the surface to which they are attached may cause different portions of these supporting elements to move in a non-linear manner with respect to the surface. This may cause unacceptable variations in the tracking results and may cause inaccuracies in what is intended to be a very accurate tracking of a respectable structure. Further, body effluent, such as sweat, will often cause deterioration of paper or cardboard elements that are exposed to it and it may even deteriorate certain kinds of cloth. On the other hand, paper or cardboard coated with a non-absorbent plastic, or the like, and that has been rendered adherent to the skin of the patient, may be well suited to use in this invention. Alternatively, supports that are made entirely of non-absorbent plastic elements, and that are adherent to the patient's skin, can be used in this invention.

In some instances, the supporting element should be relatively rigidly adhered to the underlying surface (skin) of the patient so that it will move directly with the movement of the underlying tissue that it is disposed on. However, it has been found that in some cases, a flexible material will serve very well as the supporting structure. Thus, for example, a textile fabric or a plastic film, that are suitably not adversely affected by body effluent (e.g. sweat) can be used in this service under certain conditions.

If a fabric or film is stretched to conform to a body part surface whose movements need to be tracked, it can be adhered to the surface of the body part or not, provided that it substantially continually conforms to the surface of the body part and that it continues to so conform as the patient breathes. The key property of the support element is that it accurately translates the movements of the body part to the emitter so that the emitter can transfer these exact movements to the control means that integrates these movements with the preprogrammed surgical route to form a continually changing modified surgical route, and directs the movements of the scalpel or radiation in consequence of this modified surgical route.

In a preferred aspect of this invention, where the emitter is electrically powered and is itself disposed on the surface that is subject to movement, the supporting element, whether rigid or film form, should be substantially insulating, so that the electric current that is input to cause the emitter to operate will not cause patient discomfort. Therefore, metal support elements should be used sparingly and with great care. This objection to the use of metal support elements presents a problem where the marker's location and orientation are determined as a function of a magnetic field and the magnetic elements must be magnetizable metal. In this respect, it has been found to be desirable to provide a support element that has a magnetic metal armature and an insulating cover at least over that part of the element that will come into contact with the patient's skin. Various commercially available, or yet to be invented, relatively rigid plastic materials will serve well in this function. In the case of a radiation emitter, such as a visible red, or an invisible infra red LED, the entire substantially rigid support element, or the film/fabric supporting layer, can be made of a non-conductive plastic or textile material or it may be made of metal carrying and insulating coating of insulating plastic.

In a preferred embodiment of this invention, the camera array, or other receiver, is suitably located in a fixed position, such as on the ceiling of an operating room. This position gives the greatest interference free view of the patient and the emitters that are attached to the patient. The LEDs or other emitters, including the radiating ends of the optical fibers, if that embodiment is employed, are suitably attached to wedge shaped support members so that their radiation is principally directed toward the ceiling and especially toward the camera array mounted on the ceiling. Where the camera array is mounted such that it views the patient at an angle of approximately 45°, the LED supports should cause the LEDs to emit radiation toward the camera array at a similar angle of approximately 45°. Other spatial arrangements will be apparent to those of ordinary skill in this art.

DETAILED DESCRIPTION

Figure 1A:
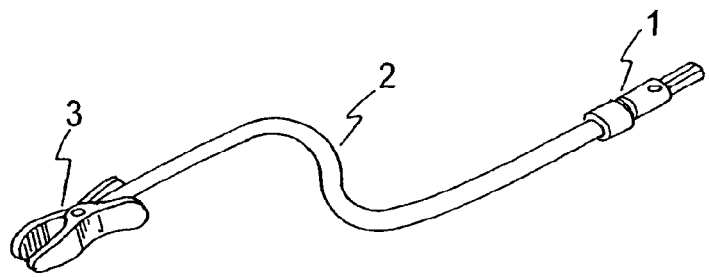
FIG. 1 (A through D) show an exploded view of the invention using a clip to connect the device with an external power source.

Referring to FIGS. 1-3, a cable 2 is adapted to be attached, at one end 1, to a source of external power (not shown) and, at the other end, to a plurality of suitable, preferably disposable, emitters 4. The emitters are shown as being attached to a supporting element 5 having one side that is suitably equipped with an adhesive material 6 that is adapted to adhere to a patient (not shown).

Figure 1B:
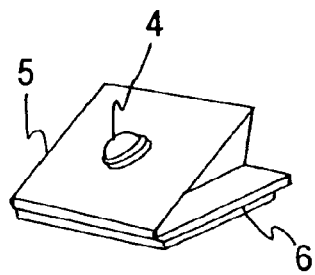
Figure 1C:
Figure 1D:
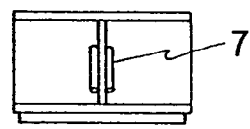

FIG. 1A is a schematic representation of one aspect of this invention that shows the cable 2 with a suitable connection, that is adapted to connect 1 to an external power supply (not shown) and a clip 3 that is adapted to connect to a lead from an LED. FIG. 1B is a schematic representation of the same aspect of this invention where there is shown an LED emitter 4 and a support element 5 with an adhesive backing 6. FIG. 1C is a schematic representation of the same aspect of this invention that shows a side view of an emitter supporting element 5 and shows a lead 7 from the LED that is adapted to be attached to the clip 3. FIG. 1D is a schematic representation of this same aspect of this invention that is similar to FIG. 1C but shows an emitter with two leads 7 extending therefrom.

Figure 2A:
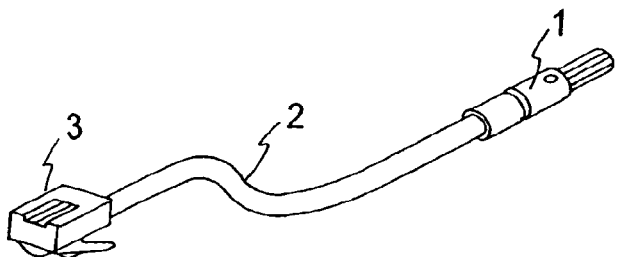
FIG. 2 (A through D) shows an exploded view of the invention using a connector to join the device (emitter) with an external power source.
Figure 2B:
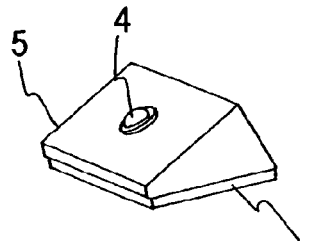
Figure 2C:
Figure 2D:
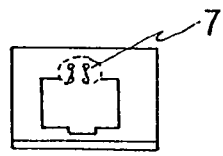

FIG. 2A is a schematic representation of another aspect of this invention that shows the cable 2 with a suitable connection 1, that is adapted to connect 1 to a power supply (not shown) and a connector 3a that is adapted to connect to a lead 7 from an LED. FIG. 2B is a schematic representation of this aspect of this invention where there is shown an LED emitter 4 and a support element 5 with an adhesive backing 6. FIG. 2C is a schematic representation of this aspect of this invention that shows a side view of an emitter supporting element 5 and shows a lead 7 from the LED that is adapted to be attached to the connector 3a. FIG. 2D is a schematic representation of this aspect of this invention that is similar to FIG. 2C but shows an emitter with two leads 7 extending therefrom for attachment to the connector 3a.

Figure 3A:
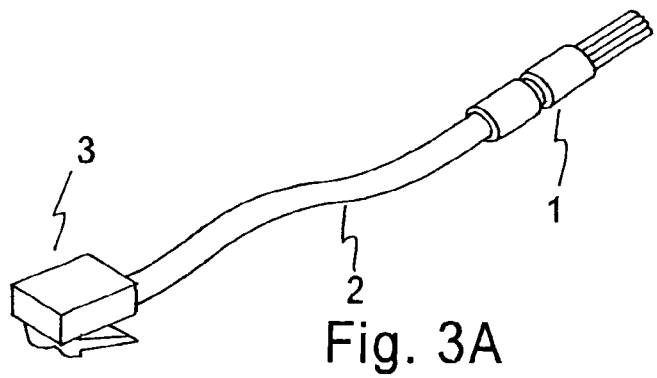
FIGS. 3 (A and B) shows an exploded view of an application of a tracking system of this invention to a patient through a film/fabric structure.
Figure 3B:
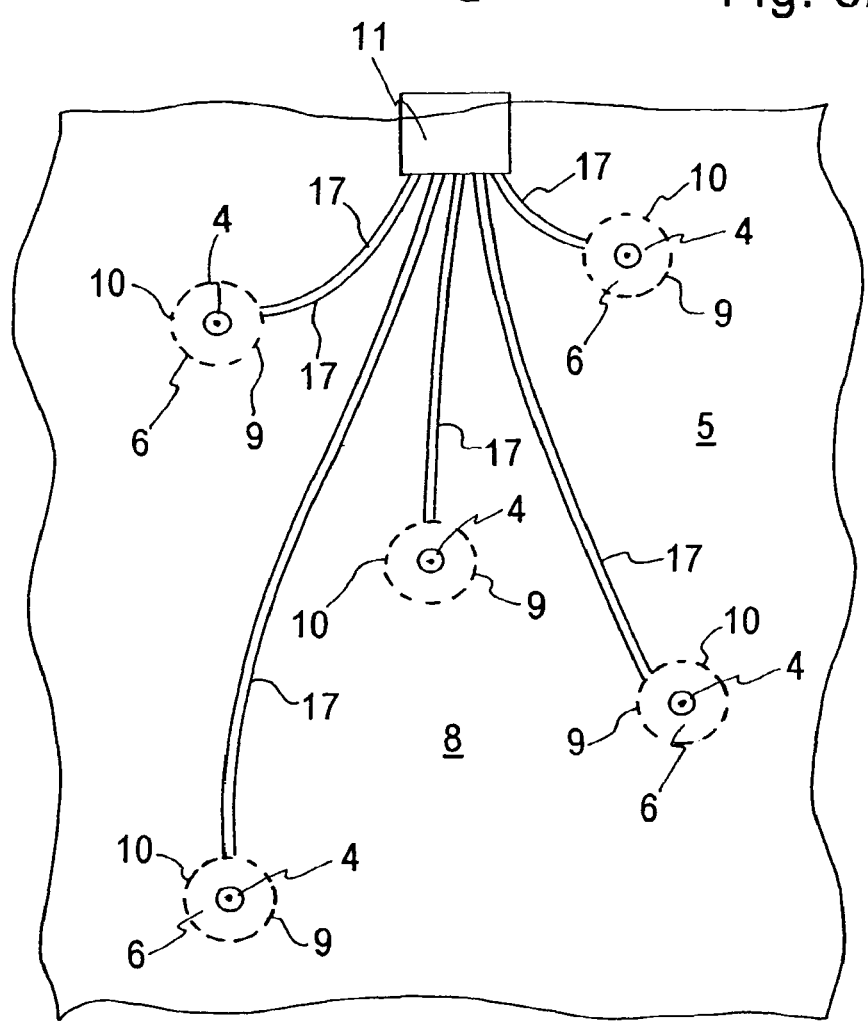

FIGS. 3A and 3B are schematic representations of a different aspect of this invention that employs a disposable fabric backing 8 to which multiple LED's 4 are attached. Each LED 4 is attached to an area 9 of the fabric under which a self-adhesive pad 10 can be disposed. It is considered to be within the scope of this invention that suitable adhesive material can be applied directly to the underlying fabric backing and to thereby enable the backing to be adhered to the body being worked on. The fabric may have suitable wiring 17 disposed on its surface and preferably attached to the fabric, or the wiring may be directly integrated into the fabric. The wiring 17 connects the several LED's to a hub 11 that is adapted to be connected to a connector 3 that is in turn connected to a power supply (not shown) though a single or multiple electrical lead 2.

Figure 4:
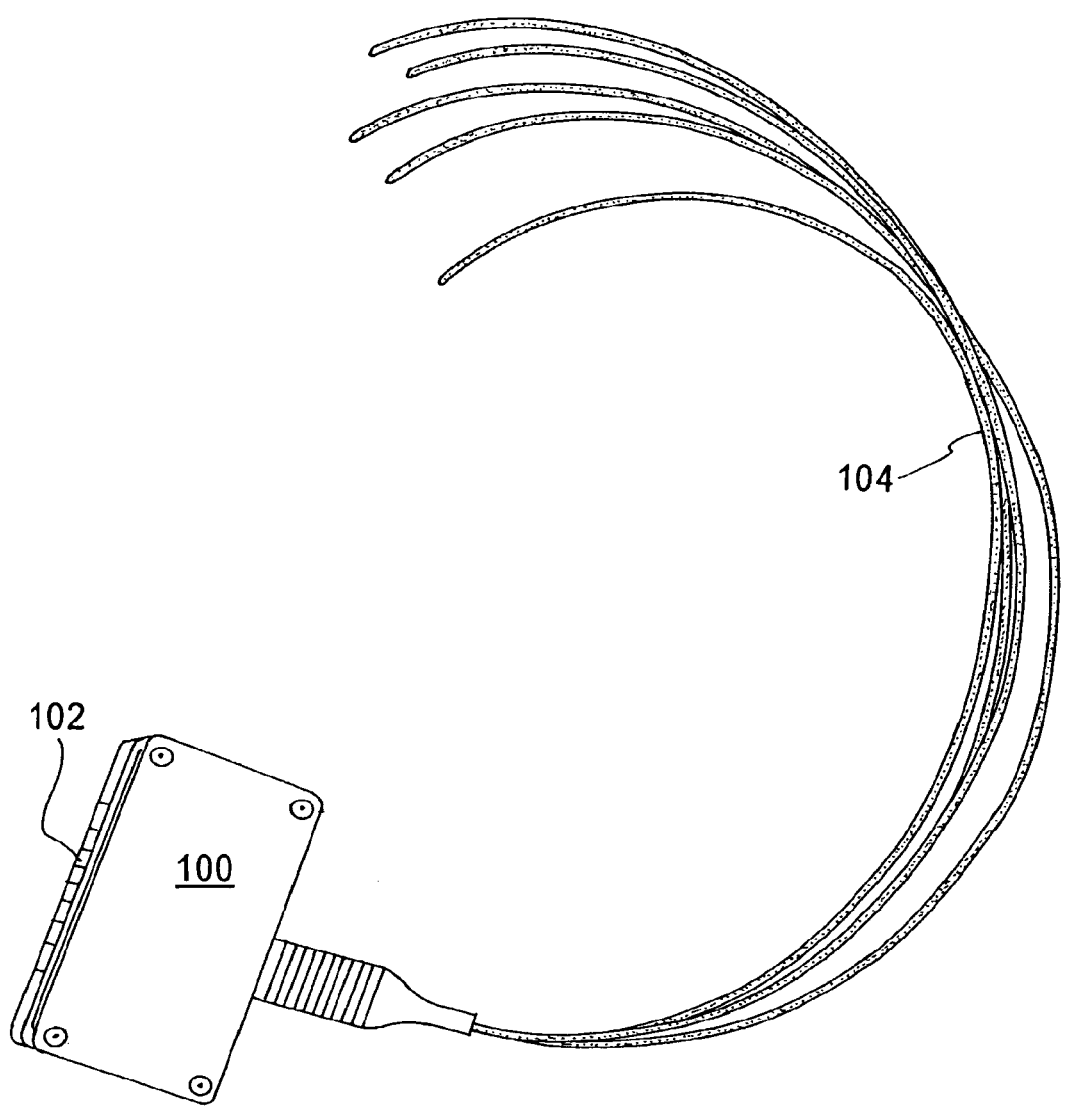
FIG. 4 is a perspective view of a remote LED housing and a plurality of optical fibers leading from that housing.

FIG. 4, shows a housing 100 in which is disposed at least one, but preferably a plurality of, LEDs (not specifically shown). Means 102 are provided to supply electric power to the LED's. A timing device (not shown) is provided operatively attached to the plural LEDs to cause the LEDs to fire in a preprogrammed sequence. A plurality of optical fibers 104, are shown emanating from the housing that are suitable for attachment to supporting means, that are, in turn, suitable for attachment to a body.

Figure 5:
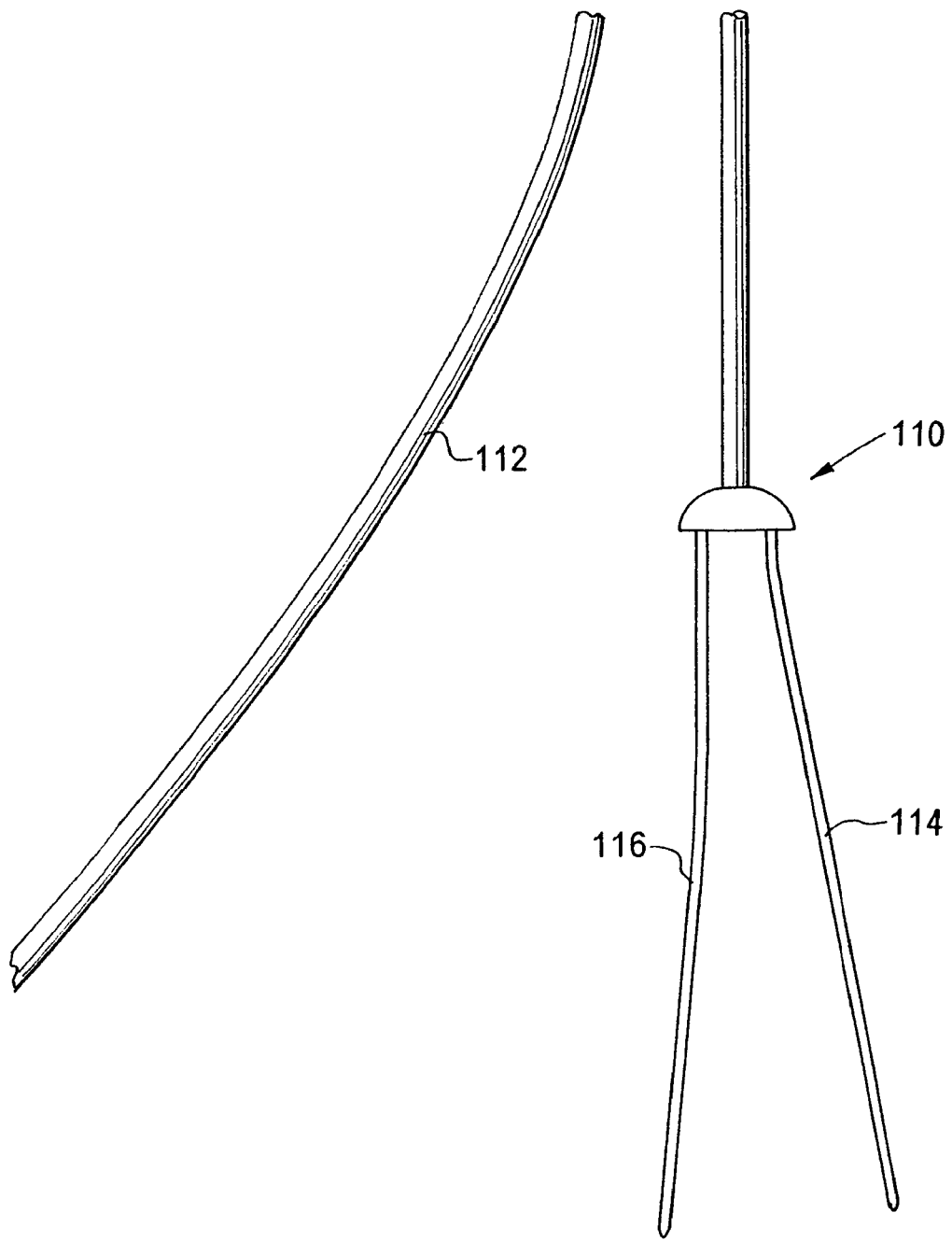
FIG. 5 is a perspective view of an LED attached to the end of an optical fiber.

FIG. 5 shows an emitting LED 110 that is attached to an optical fiber 112. The LED has two leads 114 and 116 that are attachable to a source of electric power (not shown). When the LED 110 fires, its emission is captured by the optical fiber 112 and transmitted through the fiber to a position on the outside of the patient's body being treated (not shown) from which location the emission is projected from the end of the optical fiber toward a camera array (not shown) where the movement of the skin of the patient is tracked.

What is claimed is:

1. A system for improving the accuracy of preprogrammed treatment on a body of a patient having an inside portion that is in need of the treatment and an outside portion that is moveable during the treatment, comprising:
at least one emission source;
a plurality of markers configured for independent attachment to a plurality of locations adjacent a surface of the moveable outside portion of the body proximate to the inside portion in need of the treatment to emit a corresponding plurality of signals, wherein each of the markers comprise:
a support element comprising a base for securing the marker adjacent the surface of the moveable outside portion of the body;
a signal emitter operatively associated with the support element; and an optical fiber coupling the signal emitter and the emission source;

a timing device configured to cause the signal emitters to respectively emit signals under conditions sufficient to differentiate which signal emitter is sending each signal, respectively;

at least one receiver disposed remote from the body and positioned to receive the plurality of signals from the signal emitters, wherein each of the support elements is configured to position a respective signal emitter at an angular offset from a perpendicular direction relative to the base to direct emissions from the respective signal emitter towards the at least one receiver;

a remotely-controlled surgical device;

a computing device comprising a processor and wherein the processor is configured with software executable instructions to cause the computing device to perform operations comprising:

tracking the movement of the outside portion of the body based on the received plurality of signals from the signal emitters;

identifying and mapping the inside portion of the body that is intended to be subjected to treatment;

preprogramming a treatment path adapted to be followed by the remotely-controlled surgical device; and integrating the tracked movements with the treatment path to form a modified treatment path; and a guidance apparatus configured for causing the remotely-controlled surgical device to treat the inside portion of the body along the modified treatment path while substantially preventing the remotely-controlled surgical device from departing from the modified treatment path to any substantial extent.

2. The system of claim 1, wherein the remotely-controlled surgical device is configured to be operated without benefit of a surgeon and to perform a treatment selected from the group consisting of a high energy radiation source sufficient to render the inside portion of the body necrotic and a high energy ultrasound radiation sufficient to break up stones.

3. The system of claim 1, wherein the at least one emission source comprises a plurality of light emitting diodes (LEDs).

4. The system of claim 3, wherein the timing device is configured to cause the signal emitters to respectively emit signals under conditions sufficient to differentiate which emitter is sending each signal by firing the LEDs in a predetermined sequence.

5. The system of claim 3, wherein signals from the LEDs are selected from the group consisting of emissions having wavelengths in the visible region and emissions having wavelengths in the infrared region.

6. The system of claim 3, wherein the remotely-controlled surgical device comprises a solid scalpel and wherein the at least one emission source comprises a plurality of light emitting diodes (LEDs) having emission wavelengths in the infrared region, and wherein the optical fibers comprise glass.

7. The system of claim 3, wherein the remotely-controlled surgical device comprises a high energy radiation source sufficient to render the inside portion of the body necrotic, wherein the at least one emission source comprises a plurality of light emitting diodes (LEDs) having emission wavelengths in the visible region, and wherein the optical fibers comprise plastic.

8. The system of claim 1, wherein the at least one receiver comprises an array of cameras.

9. The system of claim 1, wherein each of the support elements is configured to reposition the respective signal emitter at another angular offset from the perpendicular direction relative to the base so that a direction of emitted signals is end-user adjustable in angle relative to the bases.

10. The system of claim 1, wherein each of the support elements are disposable.

11. The system of claim 1, wherein the plurality of markers are disposable.

12. The system of claim 1, wherein each base comprises an adhesive for securing the marker to the surface of the moveable outside portion of the body.

13. The system of claim 1, wherein the remotely-controlled surgical device-is selected one from the group consisting of a surgical scalpel, an operating tool, and a surgical probe.

14. A patient movement tracking apparatus, comprising:

at least one emission source;

a plurality of markers configured for independent attachment to a plurality of locations on a surface of a moveable outside portion of a body proximate to an inside portion in need of a treatment to emit a corresponding plurality of signals, wherein each of the markers comprise:

a support element comprising a base for securing the marker adjacent the surface of the moveable outside portion of the body;

a signal emitter operatively associated with the support element, wherein each of the support elements is configured to position a respective signal emitter at an angular offset from a perpendicular direction relative to the base to direct emissions from the respective signal emitter towards the at least one receiver; and an optical fiber coupling the signal emitter and the at least one emission source; and at least one receiver disposed remote from the body and positioned to receive the plurality of signals from the signal emitters.

15. The system of claim 14, wherein the at least one receiver is configured to determine location of the plurality of markers for a remotely-controlled surgical device that is configured to be operated without benefit of a surgeon.

16. The patient movement tracking apparatus of claim 15, wherein each base comprises an adhesive for securing the marker to the surface of the moveable outside portion of the body.

17. The patient movement tracking apparatus of claim 14, wherein the at least one emission source comprises a plurality of light emitting diodes (LEDs).

18. The patient movement tracking apparatus of claim 17, further comprising a timing device configured to fire the LEDs in a predetermined sequence.

19. The patient movement tracking apparatus of claim 17, wherein signals from the LEDs are selected from a group consisting of emissions having wavelengths in the visible region and emissions having wavelengths in the infrared region.

20. The patient movement tracking apparatus of claim 17, wherein the treatment comprises a remotely-controlled solid scalpel and wherein the at least one emission source comprises a plurality of light emitting diodes (LEDs) having emission wavelengths in the infrared region, and wherein the optical fibers comprise glass.

21. The patient movement tracking apparatus of claim 14, wherein the at least one receiver comprises an array of cameras.

22. The patient movement tracking apparatus of claim 14, wherein the treatment comprises a high energy radiation source sufficient to render the inside portion of the body necrotic, wherein the at least one emission source comprises a plurality of light emitting diodes (LEDs) having emission wavelengths in the visible region, and wherein the optical fibers comprise plastic.

23. The patient movement tracking apparatus of claim 14, wherein the support elements are configured to reposition the respective signal emitter at another angular offset from the perpendicular direction relative to the base so that a direction of emitted signals from the signal emitters is adjustable in angle relative to the base.

24. The patient movement tracking apparatus of claim 14, wherein each of the support elements are disposable.

25. The patient movement tracking apparatus of claim 14, wherein the plurality of markers are disposable.

26. A plurality of disposable markers adapted for independent attachment to a plurality of locations to a surface of a moveable outside portion of a patient body proximate to the inside portion in need of a treatment to emit a corresponding plurality of signals, wherein each of the disposable markers comprise:
 a support element comprising a base for securing the marker adjacent the surface of the moveable outside portion of the body;
 a signal emitter operatively associated with the support element, wherein each of the support elements is configured to position a respective signal emitter at an angular offset from a perpendicular direction relative to the base to direct emissions from the respective signal emitter towards the at least one receiver; and
 an optical fiber coupled to the signal emitter and configured to be coupled to at least one emission source so as to communicate light signals from the at least one emission source to the signal emitter.

27. The plurality of disposable markers of claim 26, wherein the support element, signal emitter and optical fiber are configured to be compatible with a remotely-controlled surgical device that is configured to be operated without benefit of a surgeon.

28. The plurality of markers of claim 26, wherein the support elements are configured to reposition the respective signal emitter at another angular offset from the perpendicular direction relative to the base so that a direction of emitted signals from the signal emitters is adjustable in angle relative to the bases.

29. The plurality of markers of claim 26, wherein each base comprises an adhesive for securing the marker to the surface of the moveable outside portion of the body.

30. The plurality of markers of claim 26, wherein the treatment comprises a remotely-controlled solid scalpel and wherein the at least one emission source comprises a plurality of light emitting diodes (LEDs) having emission wavelengths in the infrared region, and wherein the optical fibers comprise glass.

31. The plurality of markers of claim 26, wherein the treatment comprises a high energy radiation source sufficient to render the inside portion of the body necrotic, wherein the at least one emission source comprises a plurality of light emitting diodes (LEDs) having emission wavelengths in the visible region, and wherein the optical fibers comprise plastic.

* * * * *